United States Patent [19]

Kuzma et al.

[11] Patent Number: 5,578,084

[45] Date of Patent: Nov. 26, 1996

[54] SELF-CURVING COCHLEAR ELECTRODE ARRAY

[75] Inventors: Janusz Kuzma, Lane Cove; Henry L. Seldon, Gleno Waverley; Gordon G. Brown, Parkville, all of Australia

[73] Assignees: Cochlear Ltd., Lane Cove; University of Melbourne, Parkville, both of Australia

[21] Appl. No.: 211,269

[22] PCT Filed: Sep. 25, 1992

[86] PCT No.: PCT/AU92/00517

§ 371 Date: May 4, 1994

§ 102(e) Date: May 4, 1994

[87] PCT Pub. No.: WO93/06698

PCT Pub. Date: Apr. 1, 1993

[30] Foreign Application Priority Data

Sep. 27, 1991 [AU] Australia .................... PK 8653

[51] Int. Cl.⁶ ................................................ A61F 2/18
[52] U.S. Cl. ............................................. 623/10; 607/137
[58] Field of Search ...................... 623/10; 607/116, 607/137; 128/746, DIG. 18

[56] References Cited

U.S. PATENT DOCUMENTS

| | | | |
|---|---|---|---|
| 3,751,605 | 8/1973 | Michelson | 179/107 R |
| 3,752,939 | 8/1973 | Bartz | 179/107 R |
| 4,284,085 | 8/1981 | Hansen et al. | 128/784 |
| 4,400,590 | 8/1983 | Michelson | 179/107 FD |
| 4,484,987 | 11/1984 | Gough | 204/1 |
| 4,762,135 | 8/1988 | van der Puije et al. | 128/784 |
| 4,819,647 | 4/1989 | Byers et al. | 128/642 |
| 4,832,051 | 5/1989 | Jarvik et al. | 128/784 |
| 4,898,183 | 2/1990 | Kuzma | 128/784 |
| 5,000,194 | 3/1991 | van den Honget et al. | 128/784 |
| 5,037,497 | 8/1991 | Stypulkowski | 156/245 |

FOREIGN PATENT DOCUMENTS

| | | | |
|---|---|---|---|
| 2068 | 5/1979 | European Pat. Off. | 623/10 |
| 7157 | 1/1980 | European Pat. Off. | 607/137 |
| 0124930 | 11/1984 | European Pat. Off. | |
| 0247649 | 12/1987 | European Pat. Off. | |
| 2441381 | 7/1980 | France | 623/10 |
| 2823798 | 9/1979 | Germany | 607/137 |

OTHER PUBLICATIONS

Guyton, David; "Science", vol. 131, Jul. 1973.

*Primary Examiner*—Michael J. Milano
*Attorney, Agent, or Firm*—Gottlieb, Rackman & Reisman, P.C.

[57] ABSTRACT

An electrode array (12) for cochlear (30) implant is formed by two layers, wherein the first layer (10, 20) is formed from a bio-compatible material and contains electrode contacts and connecting leads and the second layer (11, 21) is formed from a bio-compatible material having a property of a controlled rate of expansion when exposed to the water contained in body fluids. This material expands in use and curves the implanted array and enables more effective stimulation.

16 Claims, 4 Drawing Sheets

SELF-CURVING COCHLEAR ELECTRODE ARRAY

TECHNICAL FIELD

This invention relates to electrode arrays for cochlear implants.

BACKGROUND ART

Electrode arrays for insertion into the cochlea are known in various forms in the prior art. They are generally manufactured in a straight form from a resilient material. When they are inserted into the cochlea, they flexibly curve into the spiral form of the scala tympani. However, the electrode array is resilient and hence tends to "remember" its straight form, and accordingly engages the outer (radially) wall of the scala tympani. For optimum electrical stimulation to occur, it is preferred that the electrodes engage the inner wall, near the modiolus.

One solution which has been proposed is to manufacture the electrode in a spiral shape. This type of arrangement is shown in U.S. Pat. No. 4,284,085 to Hansen et al, and in the device developed by the University of California at San Francisco. However, these devices are difficult to insert in a surgical procedure, and require specialised equipment and skills to approach satisfactory performance. Moreover, they use a curve for the array which is an estimate of average shape, not the actual shape of each patient's cochlea. These devices also require very careful manufacturing techniques to produce a reliable product.

DISCLOSURE OF INVENTION

It is accordingly an objective of the present invention to provide an electrode which combines the manufacturing and insertion advantages of the straight form of electrode, while providing engagement in use with the inner wall of the canal.

The present invention accordingly provides an electrode array which after insertion curves from its original substantially linear form into a curved shape. Preferably, the electrode array is constructed from a first portion which is flexible but stable which contains the electrodes, and a second portion which is formed from material which will expand after insertion so as to curve the overall electrode into a spiral shape. Preferably, this is achieved by utilising a material which expands slowly when in contact with water, so that over a period of hours or days after insertion the electrode slowly curves inwardly so as to engage the inner wall of the canal. Hence, the optimal stimulation arrangement whereby the electrodes engage the inner wall of the canal is likely to be achieved.

BRIEF DESCRIPTION OF DRAWINGS

One embodiment of the invention will now be described with reference to the accompanying figures, in which.

DESCRIPTION OF PREFERRED EMBODIMENT

One embodiment of the invention will now be described, however, it is noted that the present invention is of wide scope and that many possible embodiments fall within the general inventive concept.

Figure 1:
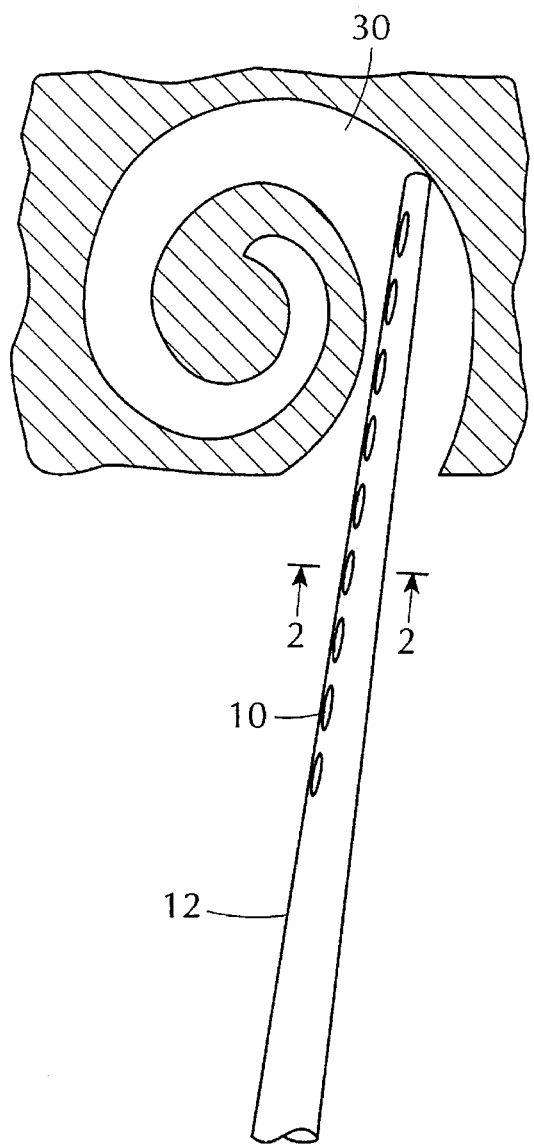
FIG. 1 is a schematic cross-sectional illustration through the plane of the cochlea showing insertion of the electrode.
Figure 4:
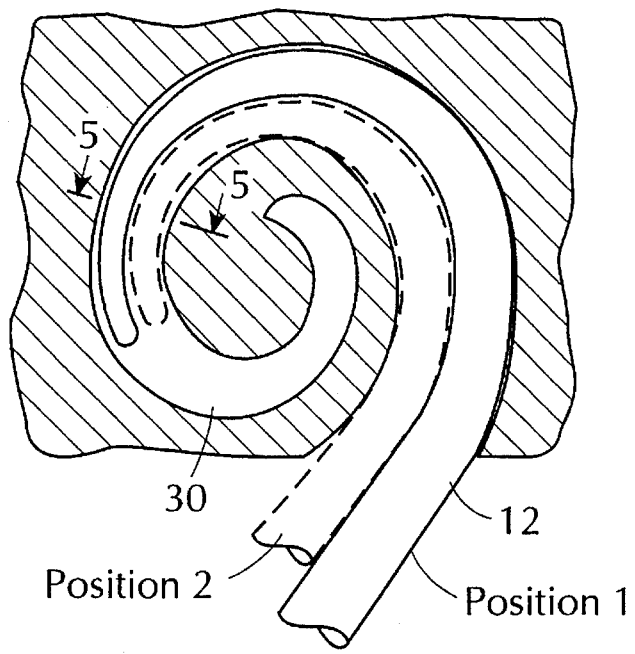
FIG. 4 is a similar view to FIG. 1 showing the positional change of the electrode array after curving.
Figure 5:
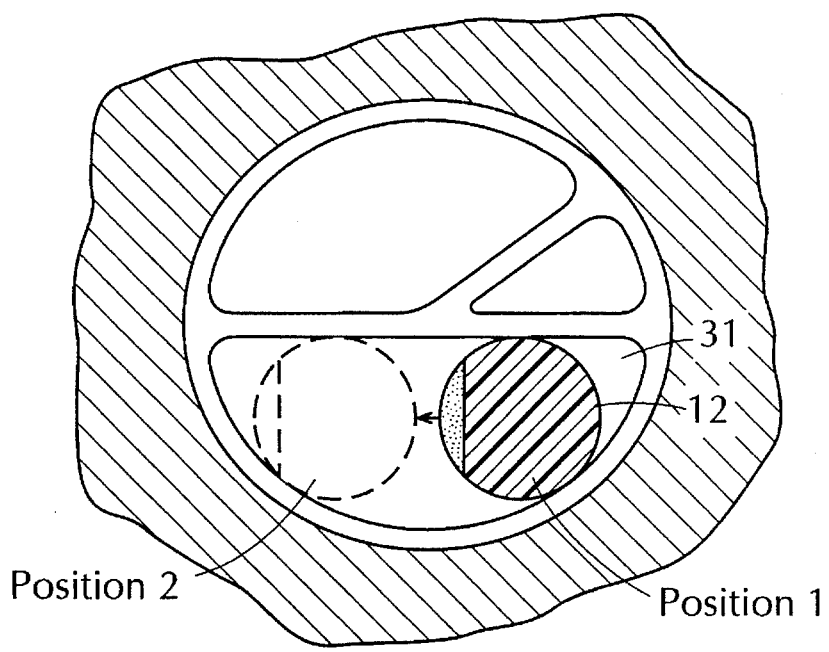
FIG. 5 is a lateral section across FIG. 4.

Referring to FIG. 1, the electrode array 12 is initially preferably formed in a generally straight cylindrical or semi-cylindrical shape. The materials are selected such that this shape will generally be maintained outside of the human body at normal conditions of temperature and humidity. In this form, it is relatively simple to control the insertion of the electrode into the cochlea 30. It will be appreciated that the illustration of the cochlea is purely schematic and is not intended to be anatomically accurate. Immediately after insertion, the electrode generally rests against the radially outer wall of the scala tympani 31, as can be seen in FIGS. 4 and 5, at position 1.

Figure 2:
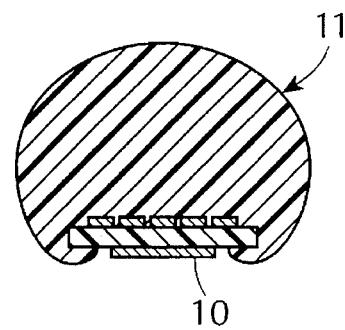
FIGS. 2 and 3 are crosssectional views along line A—A of alternative constructions of the electrode array.
Figure 3:
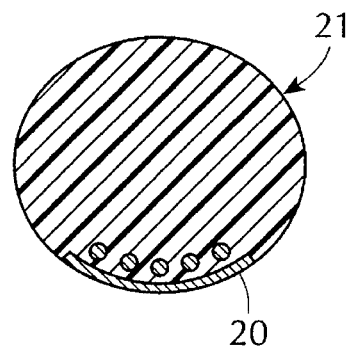

The electrode is preferably constructed in essentially two layers. Referring to FIGS. 2 and 3, the first layer (10, 20) is formed from a suitable bio-compatible material, such as a silicone polymer, and contains the electrode contacts and connecting leads in the form of a long strip structure. It is preferably constructed from a material which is flexible for bending in at least one direction, and stable in its dimensions both outside and inside the living body. In this fashion, the correct spacings between electrodes can be maintained, and the proper electrical functioning predicted accurately in use.

The second layer (11, 21) is formed from a bio-compatible material which is adhered, co-extruded or moulded to the first layer. This material has the important property of a controlled rate of expansion when exposed to the water contained in body fluids.

Any suitable water-expanding material which fulfils the above criteria may be utilised in the invention. A suitable material may be a polymer which swells in response to contact with a fluid such as water. A first preferred material is Silastic A (Trade Mark) silicone polymer mixed with a certain amount of finely ground NaCl. The exact proportion of NaCl depends on the geometry chosen and can be readily determined by those skilled in the art. A second preferred material is Silastic A mixed with polyacrylic acid to form a hygroscopic layer in the electrode structure. Both these materials will slowly expand in contact with water, thereby deforming the electrode structure from its original straight shape to a generally spiral shape with a curvature equal to or smaller than the scala tympani 31.

It will be appreciated that in its broadest form the invention encompasses alteration of shape in situ by any means, including polymers or other materials which alter their volume in response to other stimuli, such as heat or electrical stimuli, or materials which merely alter their shape so as to deform the array. It is the post insertion curving which is at the core of the present invention.

Thus, after a suitable period of time, typically hours or days, the electrode array 12 gradually moves into substantially position 2 shown in FIGS. 4 and 5. The electrodes are always positioned on their correct side because of the expansion geometry involved, so that they are in close proximity to the modiolus. It will be appreciated that the insertion is a surgical procedure and so will not always result in theoretical results, owing to differences in human anatomy, the skill and experience of the surgeon, and other factors.

Figure 7:
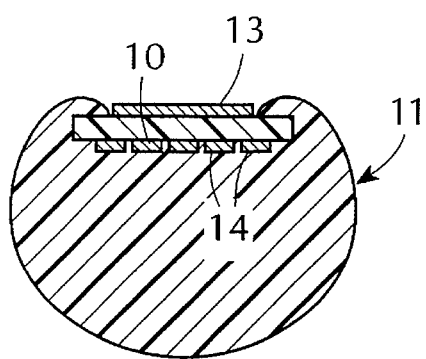
FIG. 7 is a detailed illustration of one construction of the electrode array according to the present invention.

FIG. 7 illustrates one structure incorporating the features of the present invention. A first layer 10 is constructed from a mechanically stable and bio-compatible polymer strip, with metal electrodes 13 deposited on one side and leads 14 on the other side. Any suitable material may be used for the first layer 10, although polyamide foil is preferred. The electrodes 13 and leads 14 may be formed from any suitable material, for instance sputtered platinum.

The other side of the electrode is formed from a generally semi-cylindrical portion 11 of water absorbing polymer. Preferably, the strip 10 is adhered to the material 11 during the moulding process.

Figure 8:
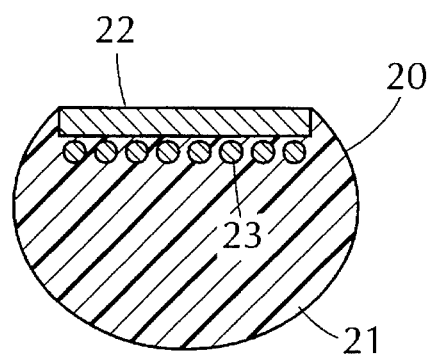
FIG. 8 is a detailed illustration of another construction of the electrode array according to the present invention.
Figure 9:
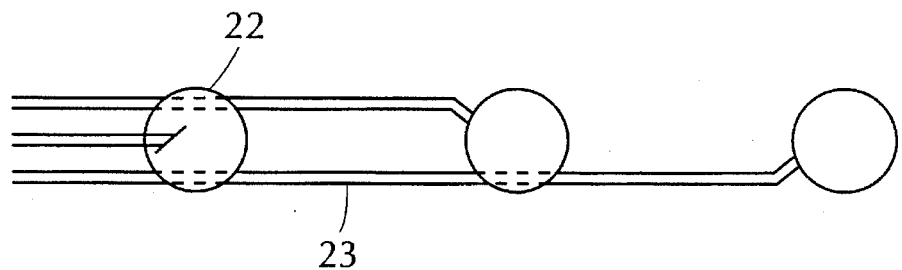
FIG. 9 shows one method for electrically connecting the electrodes according to the embodiment of FIG. 8.

FIG. 8 illustrates an alternative embodiment of the inventive structure. The first layer 20 is formed from a number of wires 23 placed side by side to form a flat ribbon connected to the platinum disk electrodes 22. This complete structure 20 is then moulded into the water absorbing polymer 21. FIG. 9 shows the connection of the discs 22 by lead wires 23.

Figure 6A:
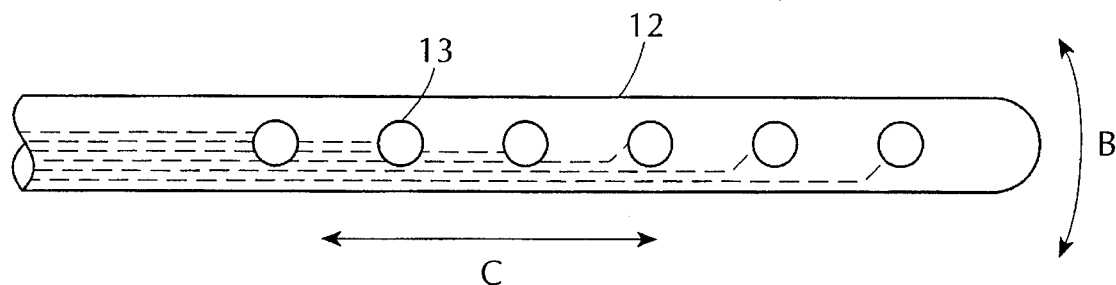
FIG. 6 shows the preferred mechanical properties required of the electrode array according to the present invention.
Figure 6B:
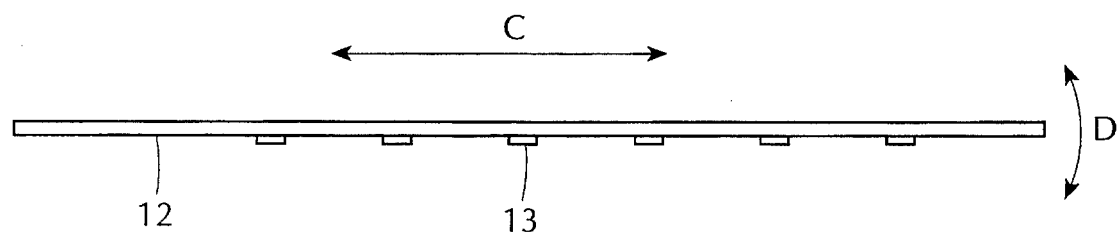
Figure 6C:

The electrode is preferably formed with mechanical characteristics as shown in FIG. 6. The electrode (in its straight form) should be flexible in a direction which is perpendicular to the plane of the electrodes, or in other words in the radial direction in the inserted structure, shown in FIG. 6 as direction D. It should, however, be stable along the plane of the electrodes, and relatively stiff across the plane of the electrodes, or in other words in directions perpendicular to the radial and coming out of the page in the illustration of FIG. 6, shown as directions B and C.

It will be appreciated that suitable polymer selection and the exact volumes of the various portions of the array will enable a suitable degree of curvature to be provided. Other differential expansion or contraction mechanisms using the same or other material properties, or other arrangements of water expanding polymer, for instance in shaped sections, are encompassed within the present invention. The array need not be precisely straight when manufactured—it may incorporate a small curve at the end to aid insertion. It will also be appreciated that embodiments are possible which do not have uniform characteristics at all points in the array.

It will be appreciated that the present invention relates to a principle of general application and the particular embodiments disclosed herein are not to be considered as limitative. Variations and additions will be apparent to those skilled in the art and are encompassed within the general scope of the invention.

I claim:

1. An electrode array for an implantable device, said array having a longitudinal axis and comprising a first portion bearing a plurality of electrodes at predetermined spacings from each other, and a second portion which is longitudinally interconnected and at least partly coextensive with said first portion, said first and second portions having respective initial volumes, and said second portion to undergo a change of volume relative to that of said first portion in a direction along said longitudinal axis, said first and second portions being disposed relatively to each other so that when the volume of said second portion changes longitudinally, at least that part of said array which includes the coextensive parts of said first and second portions inherently curves while the spacings between said electrodes borne by said first portion remain substantially constant.

2. An array according to claim 1, wherein said first portion is adapted to retain a substantially constant volume.

3. An array according to claim 1 or 2, wherein said second portion comprises a biocompatible expanding material.

4. An array according to claim 3, wherein said biocompatible expanding material of said second portion is adapted to expand when exposed to water.

5. An array according to claim 1, wherein prior to implantation of the device, said array is adapted to remain substantially stable in volume under normal conditions of temperature and humidity.

6. An array according to claim 1, wherein said array carries said electrodes on a surface, and said array is more flexible in a direction which is perpendicular to said surface than it is in a direction laterally of said surface.

7. An array according to claim 1, wherein said first and second portions are arranged longitudinally on either side of said longitudinal axis.

8. A cochlear implant device including an electrode array adapted to be inserted into the cochlea of a patient's ear, said array having a longitudinal axis and comprising a first portion bearing a plurality of electrodes at predetermined spacings from each other, and a second portion which is longitudinally interconnected and at least partly coextensive with said first portion, said first and second portions having respective initial volumes, and said second portion being adapted to undergo a change of volume relative to that of said first portion in a direction along said longitudinal axis, said first and second portions being disposed relatively to each other so that when the volume of said second portion changes longitudinally, at least that part of said array which includes the coextensive parts of said first and second portions inherently curves while the spacings between said electrodes borne by said first portion remain substantially constant.

9. A device according to claim 8, wherein said first portion of said array is adapted to retain a substantially constant volume.

10. A device according to claim 8 or 9, wherein said second portion of said array comprises a biocompatible expanding material.

11. A device according to claim 10, wherein said biocompatible expanding material of said second portion is adapted to expand when exposed to water in the patient's body fluids.

12. A device according to claim 8, wherein prior to implantation of the device into the cochlea, said array is adapted to remain substantially stable in volume under normal conditions of temperature and humidity.

13. A device according to claim 8, wherein said array carries said electrodes on a surface, and said array is more flexible in a direction which is perpendicular to said surface than it is in a direction laterally of said surface.

14. A device according to claim 8, wherein the interconnection between said first and second portions of said array is such that, upon said second portion undergoing a change of volume, the curvature assumed by said array as a whole is concave towards said first portion.

15. A device according to claim 14, wherein the curvature assumed by said array as a whole after implantation of the device into the cochlea, is such that said electrodes are disposed adjacent the radially inner wall of the cochlea within the scala tympani thereof.

16. A device according to claim 8, wherein said first and second portions are arranged longitudinally on either side of said longitudinal axis.

\* \* \* \* \*